(12) United States Patent  
Legorreta et al.

(10) Patent No.: US 7,991,626 B2  
(45) Date of Patent: Aug. 2, 2011

(54) APPARATUS AND METHOD FOR SELF-REPORTING MEDICAL INFORMATION

(75) Inventors: Antonio Legorreta, Agoura Hills, CA (US); Karen Hsu, Bend, OR (US); Zak Ramadan-Jradi, Mercer Island, WA (US)

(73) Assignee: IMS Software Services, Ltd., Wilmington, DE (US)

( * ) Notice: Subject to any disclaimer, the term of this patent is extended or adjusted under 35 U.S.C. 154(b) by 210 days.

(21) Appl. No.: 12/393,411

(22) Filed: Feb. 26, 2009

(65) Prior Publication Data

US 2009/0222287 A1 Sep. 3, 2009

Related U.S. Application Data

(60) Provisional application No. 61/032,723, filed on Feb. 29, 2008.

(51) Int. Cl.  
*G06Q 10/00* (2006.01)  
*G06F 19/00* (2006.01)  
(52) U.S. Cl. .............................................. 705/2; 705/3  
(58) Field of Classification Search .................... 705/2–3  
See application file for complete search history.

(56) References Cited

U.S. PATENT DOCUMENTS

| 7,260,480 B1* | 8/2007 | Brown et al. .................. 702/19 |
| 2006/0287885 A1 | 12/2006 | Frick | |
| 2007/0192137 A1 | 8/2007 | Ombrellaro | |
| 2008/0033751 A1* | 2/2008 | Greene .......................... 705/2 |

FOREIGN PATENT DOCUMENTS

| JP | 2008021041 | 1/2008 |
| KR | 1020020081913 | 10/2002 |
| KR | 1020070115107 | 12/2007 |
| WO | 2007139250 | 12/2007 |

OTHER PUBLICATIONS

International Search Report dated Oct. 13, 2009.

* cited by examiner

*Primary Examiner* — Luke Gilligan  
*Assistant Examiner* — Joseph Burgess  
(74) *Attorney, Agent, or Firm* — Fitch, Even, Tabin & Flannery

(57) ABSTRACT

A patient list is provided to a medical provider. The medical provider may be prompted to review particular patients on the list or they may review these patients on their own. In any case, a patient is selected from the list and the provider determines if a medical metric associated with the patient is accurate or complete. The provider may then selectively enter self-report data concerning the accuracy or completeness of the medical metric. A provider assessment (e.g., score) is recalculated based at least in part on the self-reported data as well as the data that has already been collected. The re-calculated score may be provided to the medical plan.

10 Claims, 19 Drawing Sheets

Cost of Care Key Episodes

| Quality Scorecard | Cost Score | Control Panel | Log Out |

Home >> Cost Score Summary >> Components of Cost Score

Components of Cost Score - Click Here to See all Super ETGs Composing Your Score ■ 5 Most Efficient Super ETGs

| Description | % Of Total Observed Costs | Total Episodes | Standardized Cost Score | |
|---|---|---|---|---|
| 1 Cataract | 36.0 % | 9 | -1.29 | View Detail |
| 2 Open Wound | 0.2 % | 1 | -1.16 | View Detail |
| 3 Non-macular degeneration | 0.1 % | 1 | -1.05 | View Detail |
| 4 Other a unspecified diseases and disorders of the eye and adnexa | 0.1 % | 1 | -0.83 | View Detail |
| 5 Macular degeneration | 7.2 % | 8 | -0.65 | View Detail |

■ 5 Super ETGs with the Largest Percentage of Total Costs

| Description | % Of Total Observed Costs | Total Episodes | Standardized Cost Score | |
|---|---|---|---|---|
| 1 Cataract | 36.0 % | 9 | -1.29 | View Detail |
| 2 Diabetic retinopathy | 17.0 % | 8 | 0.14 | View Detail |
| 3 Inflammatory eye disease | 16.2 % | 6 | -0.43 | View Detail |
| 4 Glaucoma, open angle | 14.1 % | 6 | 1.53 | View Detail |
| 5 Macular degeneration | 7.2 % | 8 | -0.65 | View Detail |

■ 5 Least Efficient Super ETGs

| Description | % Of Total Observed Costs | Total Episodes | Standardized Cost Score | |
|---|---|---|---|---|
| 1 Conditional exam | 5.2 % | 4 | 2.48 | View Detail |
| 2 Glaucoma, open angle | 14.1 % | 6 | 1.53 | View Detail |
| 3 Diabetic retinopathy | 17.0 % | 8 | 0.14 | View Detail |
| 4 External eye infection | 0.5 % | 2 | 0.02 | View Detail |
| 5 Non-diabetic vascular retinopathy | 3.5 % | 2 | -0.20 | View Detail |

| | Quality Scorecard | Cost Score | Control Panel | Log Out |

Home >> Clinical Quality Scorecard >> Member List

Members that did not receive the service - mmr

Members who received the service | Members who did not received the service | Eligible members

| Member ID | Date of Birth | First Name | Last Name | Report |
|---|---|---|---|---|
| 845XXXXX ←1202 | XX/XX/XXXX ←1204 | LIZXXXXX ←1206 | CARXXXXX ←1208 | Data Submitted ←1212 |
| 846XXXXX | XX/XX/XXXX | LORXXXXX | CASXXXXX | Data Submitted |
| 849XXXXX | XX/XX/XXXX | KENXXXXX | GUDXXXXX | Data Submitted |
| 848XXXXX | XX/XX/XXXX | CHRXXXXX | HERXXXXX | Data Submitted |
| U89XXXXX | XX/XX/XXXX | DAVXXXXX | LOPXXXXX | Data Submitted |
| 844XXXXX | XX/XX/XXXX | LOUXXXXX | MCCXXXXX | Data Submitted |
| 328XXXXX | XX/XX/XXXX | DAMXXXXX | MEDXXXXX | Data Submitted |
| 847XXXXX | XX/XX/XXXX | LUCXXXXX | MEZXXXXX | Data Submitted |
| 849XXXXX | XX/XX/XXXX | CAMXXXXX | MORXXXXX | Data Submitted ←1210 |
| 845XXXXX | XX/XX/XXXX | KRYXXXXX | NAMXXXXX | Add Self Report Data |

STEP 2 Displays a list of all members who did not receive the service/procedure as defined by the quality indicator. Provider clicks "Add Self Report Data" link to enter data for a particular member.

*FIG. 12*

| Quality Scorecard | Cost Score | Control Panel | Log Out |

Home >> Clinical Quality Scorecard >> Member List >> Self Report

Confirm Denominator: Date of Birth - mmr

- Provider Name   VISXXXXX
- Provider ID     35L76MA

| DOB | First Name | Last Name |
|---|---|---|
| XX/XX/XXXX | KRYXXXXX | NAMXXXXX |

← 1302

... Is the date of birth on record for this member correct?

○ Yes
○ No, member date of birth should be corrected to ☐ / ☐ / ☐ MM/DD/YYYY

[Next] [Cancel]
← 1304

STEP 3  Providers will initially be asked to confirm the member's date of birth when age is used as an inclusion criterion.

*FIG. 13*

| Quality Scorecard | Cost Score | Control Panel | Log Out |

Home >> Clinical Quality Scorecard >> Member List >> Self Report

Confirm Numerator: Vaccination - mmr

- Provider Name  VISXXXXX
- Provider ID  35L76MA

| DOB | First Name | Last Name |
|---|---|---|
| XX/XX/XXXX | KRYXXXXX | NAMXXXXX |

…Was this member vaccinated?

○ Yes, this child was vaccinated prior to December 31, 2006. Date of vaccinations provided below MMR [ ] / [ ] / [ ]　　MM/DD/YYYY　or　Measles [ ] / [ ] / [ ]　MM/DD/YYYY
　　　　　　　　　　　　　　　　　　　　Mumps　[ ] / [ ] / [ ]　MM/DD/YYYY
　　　　　　　　　　　　　　　　　　　　Rubella [ ] / [ ] / [ ]　MM/DD/YYYY　　← 1402

○ No, this child had history of disease prior to December 31, 2006

Measles [ ] / [ ] / [ ]　MM/DD/YYYY
　Mumps　[ ] / [ ] / [ ]　MM/DD/YYYY
　Rubella [ ] / [ ] / [ ]　MM/DD/YYYY ○ No, this child was not vaccinated

[ Next ]  [ Cancel ]  ← 1404

STEP 4  Providers will indicate if the member received the desired service or procedure.

*FIG. 14*

| Quality Scorecard | Cost Score | Control Panel | Log Out |

Home >> Clinical Quality Scorecard >> Member List >> Self Report

Confirm Exclusions: History of Disease or Contraindication - mmr

- Provider Name  VISXXXXX
- Provider ID  35L76MA

| DOB | First Name | Last Name |
|---|---|---|
| XX/XX/XXXX | KRYXXXXX | NAMXXXXX |

○ Had a contraindication to vaccinate prior to December 31, 2006
   ☐ HIV infected or household contact with HIV infection
   ☐ Anaphylactic reaction to neomycin    ← 1502
   ☐ Immunodeficiency of lymphoraticular or histiocytic tissue
   ☐ Multiple myeloma
   ☐ Leukemia
○ This member was deceased before December 31, 2006
○ Patient refused service or treatment
○ Other [_____]
   ← 1504
[Next] [Cancel]

STEP 5: If the date of birth is correct and providers confirm that service was not provided, the last option will be to show that the member met the denominator exclusion criteria.

*FIG. 15*

| | Quality Scorecard | Cost Score | Control Panel | Log Out |
|---|---|---|---|---|

Home >> Clinical Quality Scorecard >> Member List >> Self Report

Confirmation Page - mmr
- Provider Name  VISXXXXX
- Provider ID  35L76MA

| DOB | First Name | Last Name |
|---|---|---|
| XX/XX/XXXX | KRYXXXXX | NAMXXXXX |

... This member :  ← 1602

Had a contraindication to vaccinate prior to December 31, 2006: Immunodeficiency of lymphoreticular or histiocytic tissue Note that this member was also included as an eligible member for the following measures and will therefore be removed from the results of these measures upon confirmation.

- Childhood Immunization Varicella - Zoster Virus (VZV)

[Submit]  [Edit]
  ⌐1604

STEP 6 — Final Confirmation from the provider will be necessary to officially submit data for consideration.

*FIG. 16*

| Quality Scorecard | Cost Score | Control Panel | Log Out |

Home >> Clinical Quality Report

Clinical Quality Report
- Provider Name  PRIXXXX
- Reporting Period  2005 Program Year ⌄
- Specialty  FAMILY PRACTICE

| QUALITY | COST |
|---|---|
| 58.87 | 68.74 |
| COMPOSITE SCORE | |
| 63.81 | |

| Clinical Quality Indicator | Admin Rate | Hybrid Rate | Plan Rate |
|---|---|---|---|
| Childhood Immunization: Measles, Mumps and Rubella (MMR) | 80.0% | 100.0%<br>5/5 | 38.0% |
| • Members Who Did Not Receive the Service | | | |
| • Total Members Eligible for Service | | | |
| Childhood Immunization: Varicella – Zoster Virus (VZV) | 60.0%<br>3/5 | No Data Submitted | 39.0% |
| • Members Who Did Not Receive the Service | | | |
| • Total Members Eligible for Service | | | |
| Inappropriate Medication Use in the Elderly | 100.0%<br>2/2 | N/A | 84.0% |
| • Members Who Did Not Receive the Service | | | |
| • Total Members Eligible for Service | | | |
| Monitoring for Diabetic Nephropathy | 50.0% | 60.6%<br>40/66 | 37.0% |
| • Members Who Did Not Receive the Service | | | |
| • Total Members Eligible for Service | | | |
| Visual Field Test for Patients with Suspected Glaucoma | 100.0%<br>1/1 | N/A | 84.0% |
| • Members Who Did Not Receive the Service | | | |
| • Total Members Eligible for Service | | | |

*FIG. 17*

APPARATUS AND METHOD FOR SELF-REPORTING MEDICAL INFORMATION

CROSS REFERENCE TO RELATED APPLICATIONS

This application claims priority to Provisional Application Ser. No. 61/032,723 filed on Feb. 29, 2008 and entitled "An Apparatus and Method for Self-reporting Medical Information" the disclosure of which is incorporated by reference herein in its entirety.

FIELD OF THE INVENTION

The field of the invention relates to data reporting approaches and, more specifically, to data reporting approaches used to report medical information.

BACKGROUND

Today's health care industry is structured so that, in most cases, service providers (e.g., doctors, hospitals, other medical professionals) receive reimbursements from medical plans (e.g., private insurance plans or government-sponsored medical plans). Under these approaches, the medical plan typically determines how much to reimburse a provider for a particular procedure or service. The health plan may also determine if it even will reimburse a provider for a service and, if the service is reoccurring, how often to reimburse the provider for the service.

Quality of service concerns have been raised by many with respect to today's health care environment. Unfortunately, available methods of reimbursement have provided little financial reward for improvements in the quality of healthcare delivery. For instance, fee-for-service payments encouraged overuse while capped payments encouraged underuse, and neither approach rewarded providers based on quality. Pay-for-Performance (P4P) initiatives have been implemented in the health care industry with the intent of addressing rising healthcare costs and improving quality.

In many previous P4P approaches, the amount of reimbursement was determined by a provider performance assessment (e.g., a score). For instance, the health plan tracked the records of patients (enrolled in the health plan) and whether the provider had provided (or offered to provide) certain services for patients having a particular condition. The more patients of the provider that met the standard, the higher the score for the provider. Moreover, the higher the score, the higher the reimbursement for a provider offered by the health plan.

In some previous systems, medical chart data was sometimes used for reimbursement purposes. While medical chart data was considered an accurate source of information regarding the care provided by physicians, data collection on a wide scale for the purposes of provider performance assessment was not cost effective and placed a significant burden on providers from an administrative perspective. Hence, health plans focused on the use of administrative claims (and the data included with these claims) submitted by the provider to determine performance assessment measurements.

However, problems have arisen regarding the accuracy of using administrative claims data alone for provider performance assessment measurements. For instance, the health plan may be mistaken that a particular procedure was not performed on a patient, thus incorrectly lowering the score. In another example, a valid reason (e.g., an exclusion) may exist for not providing a service for a patient, again resulting in the incorrect lowering of the provider score. Previous approaches have not addressed these concerns.

Additionally, as P4P programs have continued to mature, providers in turn have grown in their understanding of measures, scoring practices and other program design issues. Previous systems have not been structured to provide transparency for the provider in terms of the how their assessment is calculated.

The technology used to implement previous systems has also proved problematic. For instance, in systems that use paper communications, the provider typically filed a paper request for reimbursement, this paper request was received and analyzed by the health plan, a reimbursement decision was made, and the reimbursement decision (with any reimbursement) was communicated to the provider. Unfortunately, this type of system was slow and prone to errors.

Although computer-based systems have more recently allowed data to be more quickly communicated and analyzed, these systems often required that the provider purchase custom software in order to participate and required significant time to learn. These limitations resulted in inconvenience and extra cost for the service provider.

Because of the above-mentioned problems, the frustration level of service providers has increased and the quality of service offered by the health care industry has decreased. As a result, health plans are finding it increasingly more difficult to increase or maintain provider participation and increase their quality of service.

BRIEF DESCRIPTION OF THE DRAWINGS

FIGS. 4-7 comprise screen shots of the utilization of the system of FIG. 3 for self-reporting data according to various embodiments of the present invention;

FIGS. 11-17 comprise screen shots showing the entry of self-reporting data according to various embodiments of the present invention.

Figure 1A:
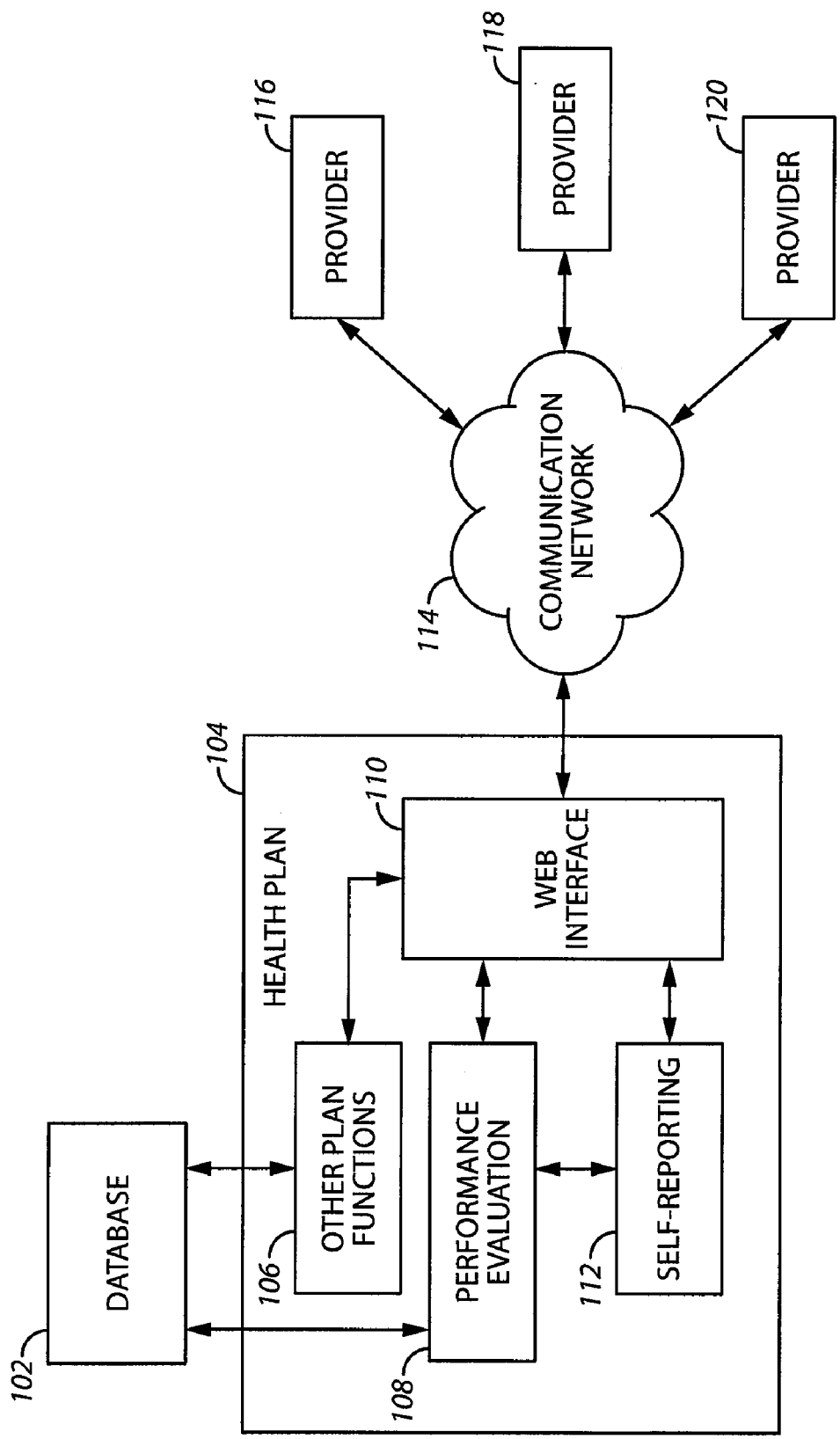
FIG. 1a comprises a block diagram of a system for self-reporting medical information according to various embodiments the present invention.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will further be appreciated that certain actions and/or steps may be described or depicted in a particular order of occurrence while those skilled in the art will understand that such specificity with respect to sequence is not actually required. It will also be understood that the terms and expressions used herein have the ordinary meaning as is accorded to such terms and expressions with respect to their corresponding respective areas of inquiry and study except where specific meanings have otherwise been set forth herein.

DESCRIPTION

Approaches are provided for the self-reporting of data from a medical provider and the calculation and distribution of a provider assessment. The self-reporting approaches described herein provide transparency for providers to examine how assessments are determined and provide for a quick and convenient mechanism for these providers to update and improve their assessments. In so doing, the attractiveness of medical plans and provider participation in these plans is enhanced and increased. The self-reporting approaches described herein are convenient for providers to use, do not require providers to purchase or install additional or costly software, are constantly available, and provide for the secure storage and use of confidential and sensitive patient information. A two-way communication procedure between the provider and health plan is supported.

In many of these embodiments, a patient list is provided to a medical provider. The medical provider may be prompted to review the records of particular patients on the list or may retrieve and review the records of these patients on their own initiative. In any case, a patient is selected from the list and the provider determines if a medical metric associated with the patient is accurate or complete. The provider may then selectively enter self-report data concerning the accuracy or completeness of the medical metric. A provider assessment (e.g., a score) is recalculated based at least in part on the self-report data as well as the data that has already been collected. The re-calculated score may be then provided to the medical provider.

The self-reporting approaches describe herein address concerns about the limitations of administrative claims data for provider assessment (e.g., score determination). More specifically, these approaches allow providers to enter self-report data regarding various metrics (e.g., clinical quality indicators) to supplement the other data that is available through the administrative data received by the health plan. In some examples, the providers may be given a set time period (e.g., 60 days), during which they can review the medical chart of those members that were identified by the health plan as having service gaps relating to the selected indicators. If there is evidence that the patient (i.e., member of the health plan) met certain exclusion criteria or indeed received the indicated service or procedure, the provider can use this time period to report this information. Data that is captured through this process is incorporated into the processing steps so that a "hybrid assessment" (e.g., a hybrid score), which includes self-reported and administrative claims data, can be made and this hybrid assessment can be reported to the provider.

These approaches are accessible via different communication networks (e.g., an Internet connection) at all times (i.e., 24 hours a day, 7 days a week, 365 days a year). Because there are no client side software requirements on the provider side, providers can login to the system from their office, home, or any other location where an appropriate communication link or connection (e.g., an Internet connection) is available.

These approaches also provide a repository for historical performance results. Thus, there is no need to keep track of paper based reports over time, which can often be misplaced. By simply selecting a measurement period from a menu of reports, providers can view their most recent reports or go as far back in time as needed to evaluate performance over time.

The approaches described herein also have the ability to provide access to program information metrics (or indicators) including indicator descriptions, terms and definitions, and summaries of how scores are derived. Not only do providers benefit by having all key reports and documentation in one place, but health plans also reduce the need to generate and distribute these materials over time.

Providers can additionally view personal performance results for both clinical quality and cost of care. Many of these approaches are implemented as an Internet-based application that enables providers to login through a secure system to view their own personalized performance results for both clinical quality and cost of care. These approaches report performance data to providers that is accurate, actionable and clinically relevant.

The information can be used for various other purposes. For example, providers can download a list of members (patients) into a disease management system or target members for specific interventions. Other uses for the information are possible.

Enhanced security is also provided with the present approaches. For instance, providers may have an assigned username and password to access the application, which utilizes secure socket layer (SSL) and encryption to secure transmission. In some examples, a role based security system is utilized to ensure that providers can only view their own performance results. Thus, using these approaches, health plans no longer need to worry about paper reports being delivered to the wrong provider or being misplaced. This is particularly relevant if providers request a listing of members for which service gaps were identified.

The hardware/software utilized to implement these approaches can be offered as a standard alone application where providers receive a uniform resource locator (URL) and login with a username and password. In addition, health plans that have an existing provider portal can make the system available to providers using a single sign-on approach.

These approaches provide the ability to create, store, maintain, and view historical reports so that providers can access to compare performance over time. A trend graph can be constructed to help summarize the performance of the provider over time by metric.

Referring now to FIG. 1a, one example of a system for self-reporting medical data is described. A health plan 104 is connected to a database 102 and to providers 116, 118, and 120 via a communication network (e.g., the Internet) 114. The health plan 104 includes a performance evaluation module 108, a self-reporting module 112, a network interface 110 and other functions module 106. It will be appreciated that the performance evaluation module 108, self-reporting module 112, and network interface 110 may be implemented as some combination of computer software instructions executed on a processing device (e.g., a microprocessor, general purpose computer, or the like). In other examples, some or all of these modules may be implemented primarily as electronic hardware.

The database 102 may be any type of memory storage device. For example, the database 102 may be a random access memory (RAM), read only memory (ROM), programmable read only memory (PROM), or any other type of memory device. The database 102 holds administrative data previously calculated and the self-report data as it is received from the providers 116, 118, and 120. Various reports analyzing both the administrative data and/or self-report data may be stored for historical evaluation purposes.

The providers 116, 118, and 120 represent any type of professional medical service provider such as doctors or hospitals. The providers may access the communication network 114 via any type of electronic device and/or interface using any type of communication technology or protocol. For example, the providers 116, 118, 120 may use personal computers, personal digital assistants (PDAs), cellular phones, or the like to access the communication network 114.

The communication network 114 is any type of network such as the Internet, a cellular communication network, or a satellite communication network. In addition, the communication network may be combinations of these networks. These networks may transmit and receive information according to any type of protocol or standard.

Turning now to the components of the health plan 104, the performance evaluation module 108 evaluates the performance of different providers and determines an assessment of this performance. For example, the assessment may be calculated by a formula that divides a denominator into a numerator. In one example, the denominator indicates the number of patients in the patient pool (for a particular provider), and the numerator the indicates the number of patients that have received particular services (for a particular provider). For example, the denominator may indicate the number of children patients and the numerator may indicate the number that have received the MMR vaccine. The assessment (e.g., score) is determined my dividing the numerator by the denominator. Other examples of assessment formulas are possible.

The self-reporting module 112 may generate self-report display screens or questions that are forwarded to the provider 116, 118, or 120 via the network interface 110. The self-reporting module 112 may also receive self-report information from the providers 116, 118, or 120 via the network interface 110.

The self-report information can relate to any type of medical metric (or indicator). The medical metric represents a service, treatment, or some other medical indicator received, associated with, or given to a patient. For example, the medical metric can relate to childhood immunizations such as measles, mumps and rubella (MMR) or the Varicella-zoster virus (VZV) vaccine and whether a patient has received these vaccinations. In another example, the metric may be related to diabetes care such as the diabetic retinal exam, the lipid panel for diabetes, screening for diabetic nephropathy, or HbA1C testing for diabetes and whether a patient has received these services. In yet another example, the metric is related to preventive screening such as colorectal cancer screening, cervical cancer screening, mammography screening, or Chlamydia screening and whether the patient has received these services. Other examples of metrics are possible.

After receiving the information, the self-reporting module 112 may analyze this information (e.g., determine the type of information received and whether a new assessment will be determined). If a new assessment is to be determined, it may supply information to the performance evaluation module 108 or, alternatively, it may determine the assessment itself. Once the new assessment is made, the self-reporting module 112 may communicate this information to the providers 116, 118, or 120 via the network interface 110 and network 114.

The self-reporting module 112 may also determine that there are service gaps for particular patients. For example, the self-reporting module 112 may determine that for a given condition, various treatments are required and that for particular patients of particular providers, gaps in service exist. The existence of gaps may be communicated to the appropriate providers 116, 118, or 120 via the network interface 110 and the provider 116, 118, or 120 may respond to these gaps with self-report data.

The network interface 110 is configured and adapted as an interface between the network 114 and the modules within the health plan 104. In this regard, the network interface 110 receives information according to a network protocol or standard and converts this information in a form that is usable by the remaining modules of the health plan 104. In another example, the network interface 110 receives information from the modules within the health plan 104 and transmits and performs any needed conversions of this information so that this information can be transmitted over the communication network 114.

The network interface 110 may also be configured to provide various security functions. For instance, providers 116, 118, and 120 may have an assigned username and password to access the other health plan modules, which utilizes secure socket layer (SSL) and encryption to secure transmission. In some examples, a role based security system is utilized to ensure that providers 116, 118, and 120 can only view their own performance results.

The other functions module 106 may provide other services for the health plan 104. For example, the other functions module 106 may supply survey questions to the providers 116, 118, or 120. In another example, the other functions module 106 may receive other types of inquiries from the providers 116, 118, or 120 and respond to these inquiries accessing the database 102 as needed to provide the answers to the inquiries from providers. Reminders and/or other search functions may be provided that allow providers to see all the service gaps for a given member.

In one example of the operation of the system of FIG. 1, providers 116, 118, and 120 may login to the health plan 104 via the communication network 114 and by using the network interface 110. The interface 110 provides security to only allow authorized users access to the health plan 104. The performance evaluation module 108 may determine preliminary results using administrative data stored in the database 102 and present these to the providers 116, 118, and 120.

The self-reporting module 112 may determine that there are service gaps for patients of particular providers and then sends this information to the providers 116, 118, or 120. This information may be sent to providers 116, 118, and 120 by the interface 110 and network 114. Alternatively, the providers 116, 118 and 120 may access their quality of service information and request to enter self-reporting data. The self-report data is received at the interface 110 and forwarded to the performance evaluation module 108 either directly or via the self-reporting module 112. The performance evaluation module 108 may recalculate the assessment (e.g., score) for the provider 116, 118, or 120 and this may be sent to the provider using the network interface 110 via the communication network 114. The provider 116, 118, or 120 can then view this information.

Figure 1B:
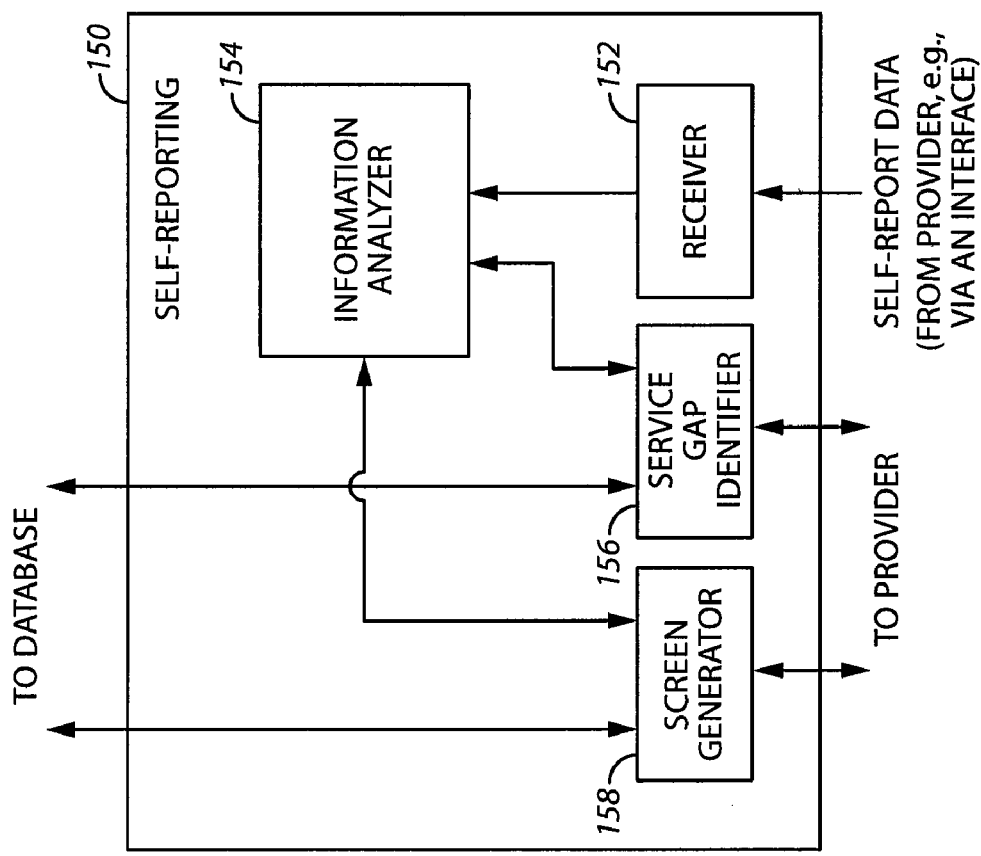
FIG. 1b comprises a block diagram of a self-reporting module according to various embodiments of the present invention.

Referring now to FIG. 1b, one example of a self-reporting module 150 (e.g., the self-reporting module 112 of FIG. 1a) is described. The module 150 and its components may be implemented as some combination of electronic hardware and/or software components. For example, the module 150 and its components may be implemented as computer executed instructions that are executed on a processing device (e.g., a microprocessor, general purpose computer, or the like).

It will be appreciated that the structure indicated in FIG. 1*b* is one example of a self-reporting module and that other examples are possible. In this case, the module 150 includes a receiver 152, an information analyzer 154, a screen generator 156, and a service gap identifier 158. The service gap identifier function may also be provided at a performance evaluation module (e.g., the performance evaluation module 108 of FIG. 1).

The receiver 152 receives self-report information from users. For example, the receiver 152 may having buffering capabilities and receive information from an interface (e.g., network interface 110 of FIG. 1*a*).

The information analyzer 154 may analyze the received information to extract the self-report data. The information analyzer 154 may also receive information (e.g., administrative data that may include information submitted in claims or from medical charts) from a database (e.g., the database 102 of FIG. 1*a*). Based upon the information received (self-reported by the provider and/or administrative data stored), the information analyzer 154 may determine particular questions to present to the user. The information analyzer 154 may send information on to a performance evaluator (e.g., the performance evaluation module 108 of FIG. 1*a*) to determine an assessment that takes into account the self-report data. Alternatively, the information analyzer 154 may perform this function itself. The information analyzer 154 may perform other functions as well.

The screen generator 156 generates self-report display screens to be sent to a provider. The screen generator 156 may receive information from the information analyzer 154 instructing the screen generator 156 to construct and send to a provider a particular customized display screen. For example, the screen generator 156 may determine a display screen or series of display screens communicating questions relating to childhood vaccinations to a provider.

The service gap identifier 158 identifies gaps in service for particular patients. The service gap identifier 158 receives information from the information analyzer 154 and/or a data storage device (e.g., the database 102 of FIG. 1*a*) and determines for a particular patient and provider if gaps in services exist. For example, the service gap identifier 158 may identify all children patients and determine for each child if a particular metric (e.g., a particular immunization) has been performed. The service gap identifier 158 may indicate service gaps to providers, for example, by sending an email to the service provider.

Figure 2A:
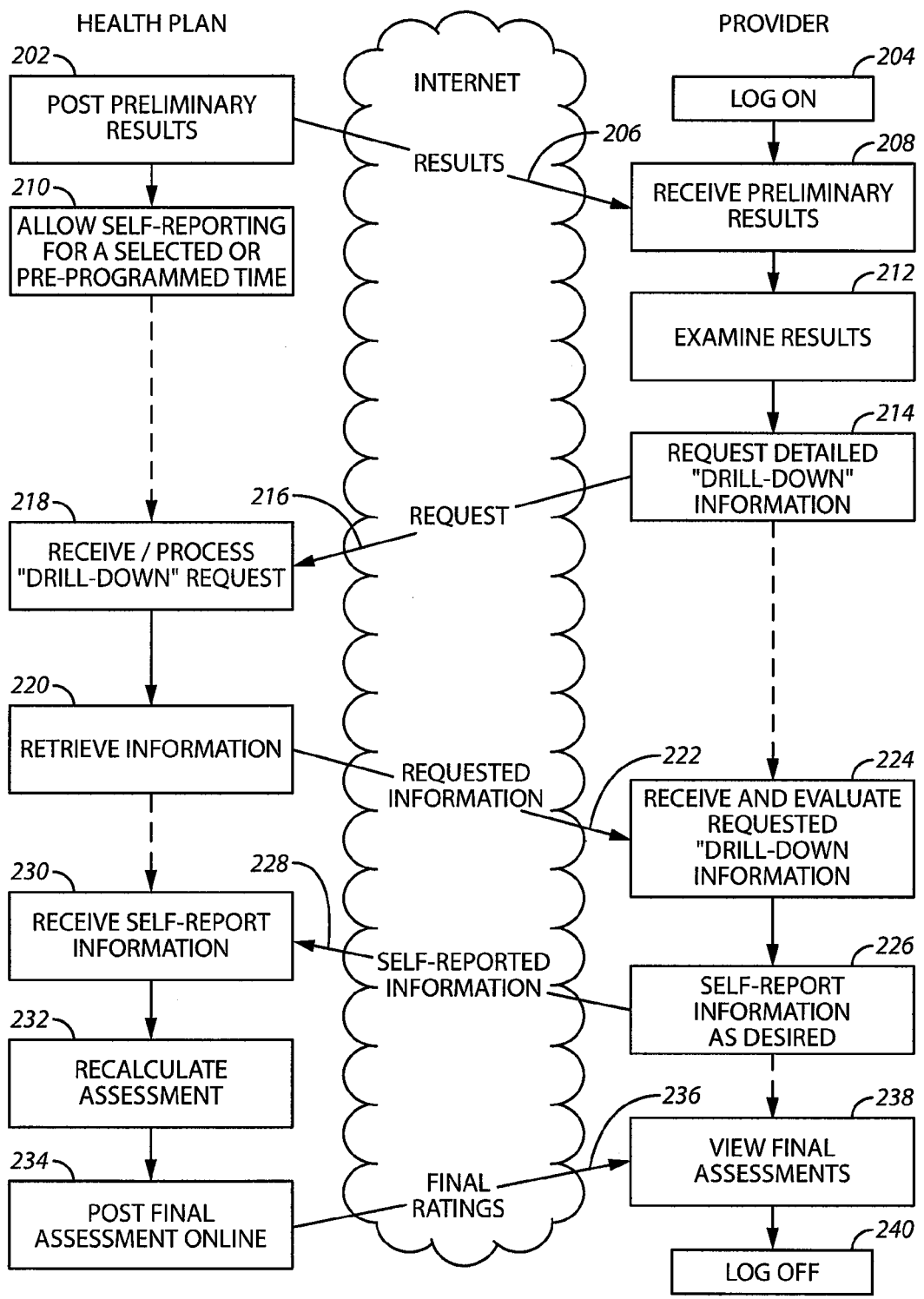
FIG. 2a comprises a flow chart of an approach for self-reporting data according to various embodiments of the present invention.

Referring now to FIG. 2*a*, an approach for self-reporting data is described. At step 202, preliminary results (e.g., an initial assessment not based upon any self-report data that only includes administrative data) are posted for providers. As mentioned, these initial assessments are based on the administrative data that has been received and processed by the health plan. At step 204 the provider logs in to the system. At step 206, the preliminary results of the assessment are sent to the provider. At step 208, the preliminary results are received by the provider.

At step 210, the health plan allows self-reporting for a selected or pre-programmed period of time. For example, the health plan may allow 60 days for providers to enter self-report data. Shorter or longer periods may also be used. At step 212, the provider examines the preliminary results that have been posted. At step 214, the provider requests more detailed "drill down" information regarding a patient associated with the results. The drill down information may be selected and retrieved by the provider selecting a link on a computer display screen. The selection of a link causes the formation of a request for the more detailed drill down information and at step 216, this request for the more detailed drill down information is sent to the health plan. At step 218, the request is received at the health plan.

At step 220, the requested information is retrieved, and at step 222, the information is sent to the provider. At step 224, the requested information is received and evaluated by the provider. At step 226, the provider determines to self-report some information and enters this information. At step 228, the self-report information is sent to the health plan. At step 230, the self-report information is received at the health plan and, at step 232, the health plan recalculates the assessment based on the self-report data. Alternatively, another entity may recalculate the assessment and receive the needed information to perform the recalculation.

At step 234, the final ratings including the recalculated ratings are posted and at step 236 sent to the provider. At step 238 the recalculated assessment is received and displayed for viewing by the provider. At step 240, the user logs off.

Figure 2B:
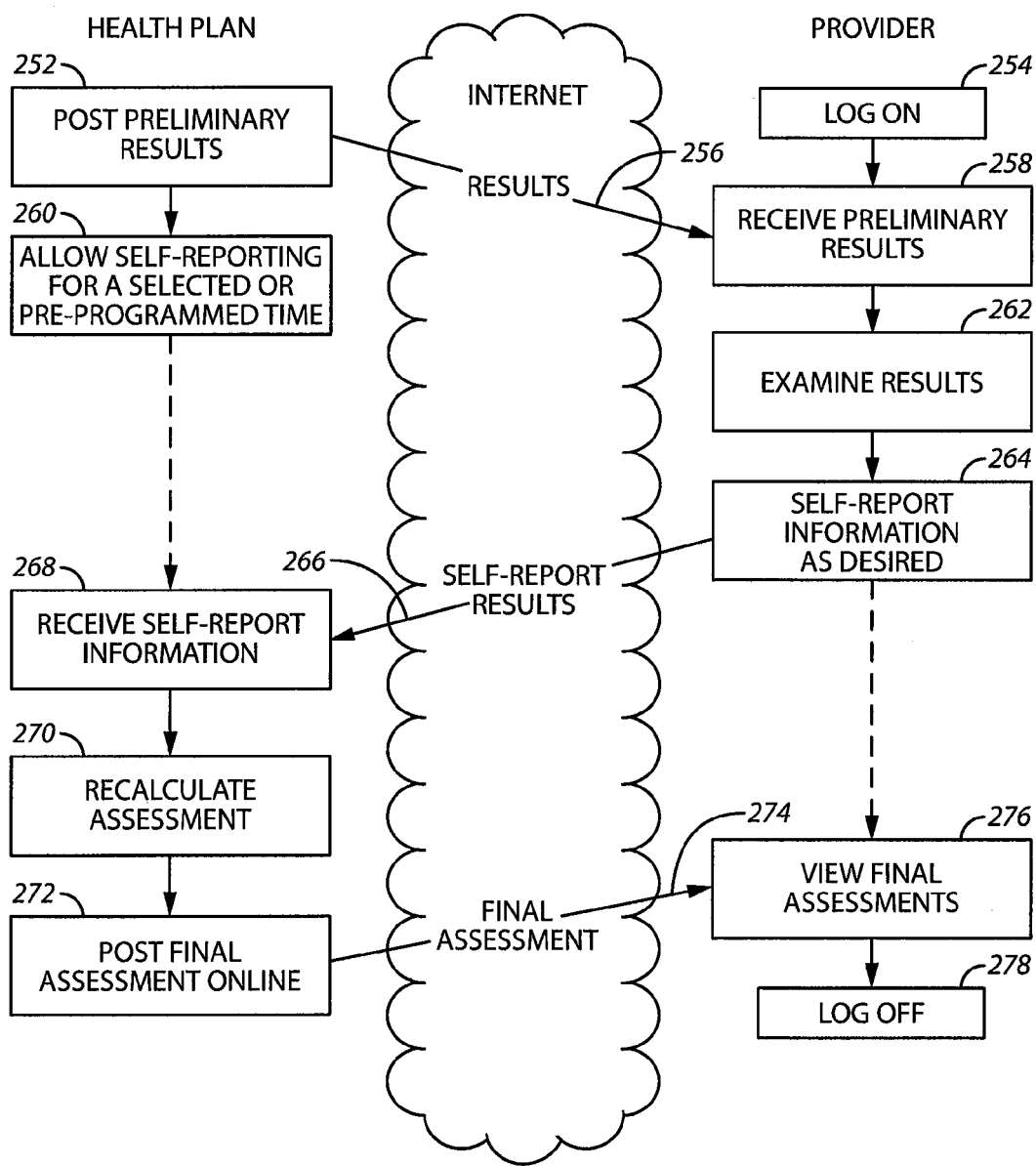
FIG. 2b comprises a flow chart of an approach for self-reporting data according to various embodiments of the present invention.

Referring now to FIG. 2*b*, another example of an approach for self-reporting data is described. At step 252, preliminary results are posted for providers. These are based on the administrative data that has been received by the health plan. At step 254 the provider logs in. At step 256, the preliminary results are sent to the provider. At step 258, the preliminary results are received by the provider. In other examples, the health plan may send a message or messages to the provider (e.g., via email) alerting the provider that gaps exist in the service for particular patients.

At step 260, the health plan allows self-reporting for a selected or pre-programmed period of time. For example, the health plan may allow 60 days for providers to enter self-report data. Shorter or longer periods may also be provided. At step 262, the provider examines the preliminary results.

At step 264, the provider determines to self-report some information and enters this information. At step 266, the self-report information is sent to the health plan. At step 268, the self-report information is received at the health plan and at step 270, the health plan recalculates the assessment based on the self-report data. Alternatively, another entity may recalculate the assessment.

At step 272, the final ratings including the recalculated assessment posted and at step 274 sent to the provider. At step 276 the recalculated assessment is received and displayed for viewing by the provider. At step 278, the user logs off.

Figure 3:
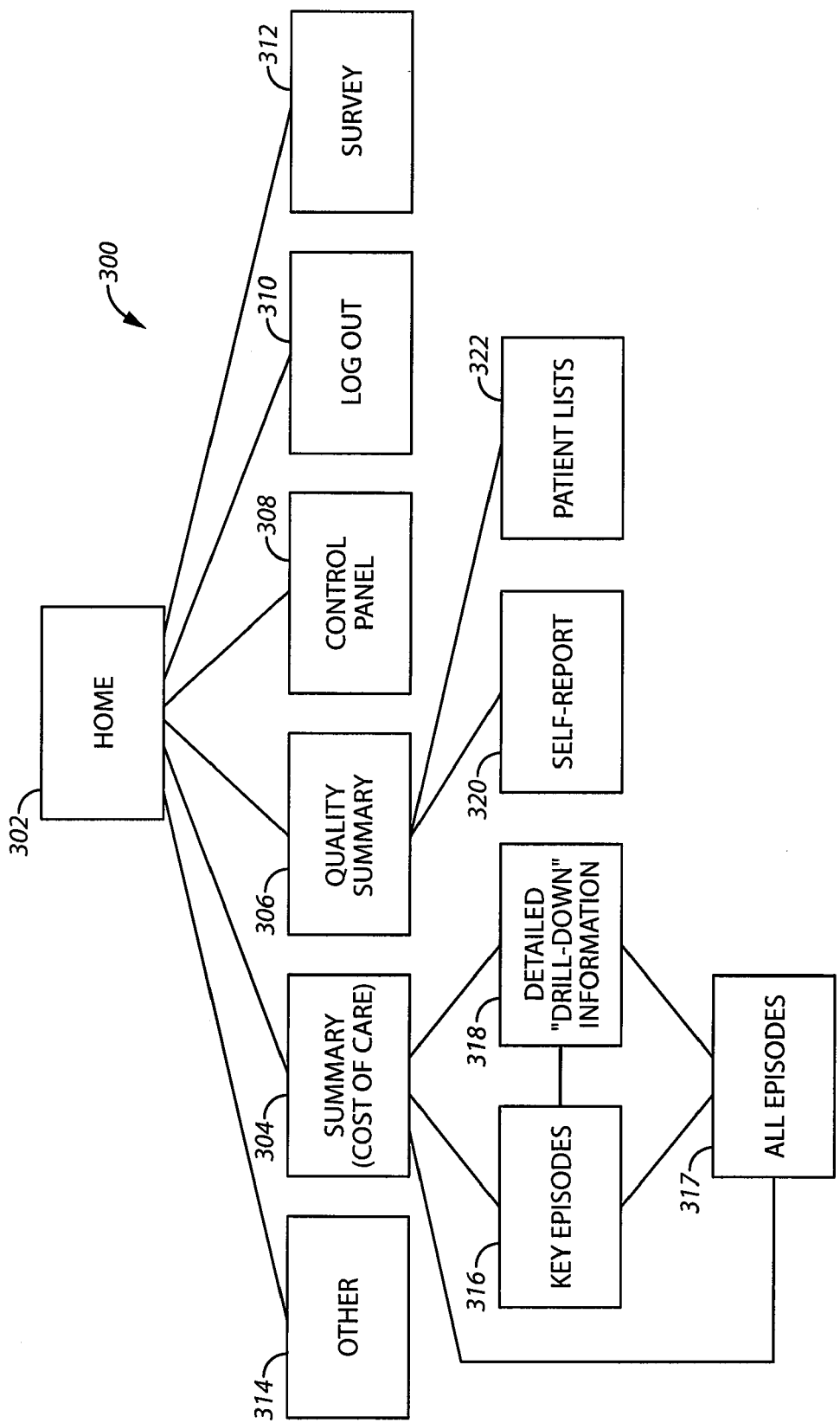
FIG. 3 comprises a block diagram of a system that allows self-reporting of data according to various embodiments of the present invention.

Referring now to FIG. 3, one example of a structure for a system 300 that provides the ability to self-report medical data to a health plan is described. The system 300 has a home display screen 302 where the user (e.g., a service provider) may log in and, after login select a variety of different display screens/functions or other options. In this example, the display screens or functions that may be selected by the user include a summary (cost of care) screen 304, a quality summary screen 306, a control panel screen 306, a logout screen 310, a survey screen 312, and an other screen 314. As described below, the screens include various links that can be used to display or access various types of information or proceed to other screens or functions. Other examples of screens are possible. For instance, screens may be provided to access historical archives of information. It will also be understood that in this example, a web interface accessible via the Internet is used to provide the display screens. However, it will be appreciated that these screens or functions may be provided on any type of electronic device such as a cellular phone or a PDA.

The summary (cost of care) screen 304 provides cost summary information for the different procedures or services performed by the provider. Links on this screen allow a key episodes screen 316 to be viewed. The key episodes screen 316 allows a provider to view components of the cost score. The key episodes screen may show the most and least efficient groups of data, such as those produced by the Episode Treatment Grouping® (ETGs®) tool supplied by Ingenix, Inc. In one example, an episode includes all clinically related service for a discrete diagnostic condition from the onset of symptom to the completion of treatment. All episodes of similar types are associated with a treatment group like Diabetes, Asthma or any other diagnoses.

Links on the screen 304 also allow a detailed drill down screen 318 to be viewed. More specifically, different types of cost information for particular clinical procedures may be viewed. For example, for an ophthalmology specialty, cost information for the eye procedure, anesthesia, and out patient services is displayed. A provider average score, specialty average score, percent of episode cost are also displayed.

Links on the screen 304 allow an all episodes screen 317 to be viewed, which shows a list of all episodes for a provider. Detailed drill down information can be obtained from the key episodes screen 316 and the all episodes screen 317.

The quality summary screen 306 shows a summary of the provider's quality assessment information. Through this screen, the user can select a link that activates the self-report screen 320 or a patients list screen 322. The self-report screen 320 allows the provider to enter self-report information. The patients list screen 322 includes patients that received and did not receive service.

The control panel 306 allows the user to select different control settings. For example, the user may be able to select different display parameter links such as the format of the information to be displayed or the amount of information to be displayed. Once these parameters are selected, they may be adjusted as needed by the user. Password administration may also be provided.

The logout screen 310 allows the user to logout. For example, a link may be selected by the user that logs the user out of the system. A screen stating that the user has successfully logged out may also be displayed.

The survey screen 312 allows the provider to take part in or view a survey. For example, information relating to the waiting time for a patient to be seen, time spent by provider with patient, or bedside manners may be obtained.

The other screen 314 allows for the provision of other functions that are not listed above and/or are added at a later date. For example, a message center may indicate messages received from the provider (e.g., indicating service gaps for particular patients). New features may be added to the system and accessed using links on this screen.

Referring now to FIGS. 4-7, examples of display screens that may be provided are described. It will be understood that these are one example of a sequence of screens a user can be presented and that other sequences are possible. It will also be understood that the contents of the screens may also differ and that other examples are possible based upon the requirements of the system or the users of the system.

Figure 4:
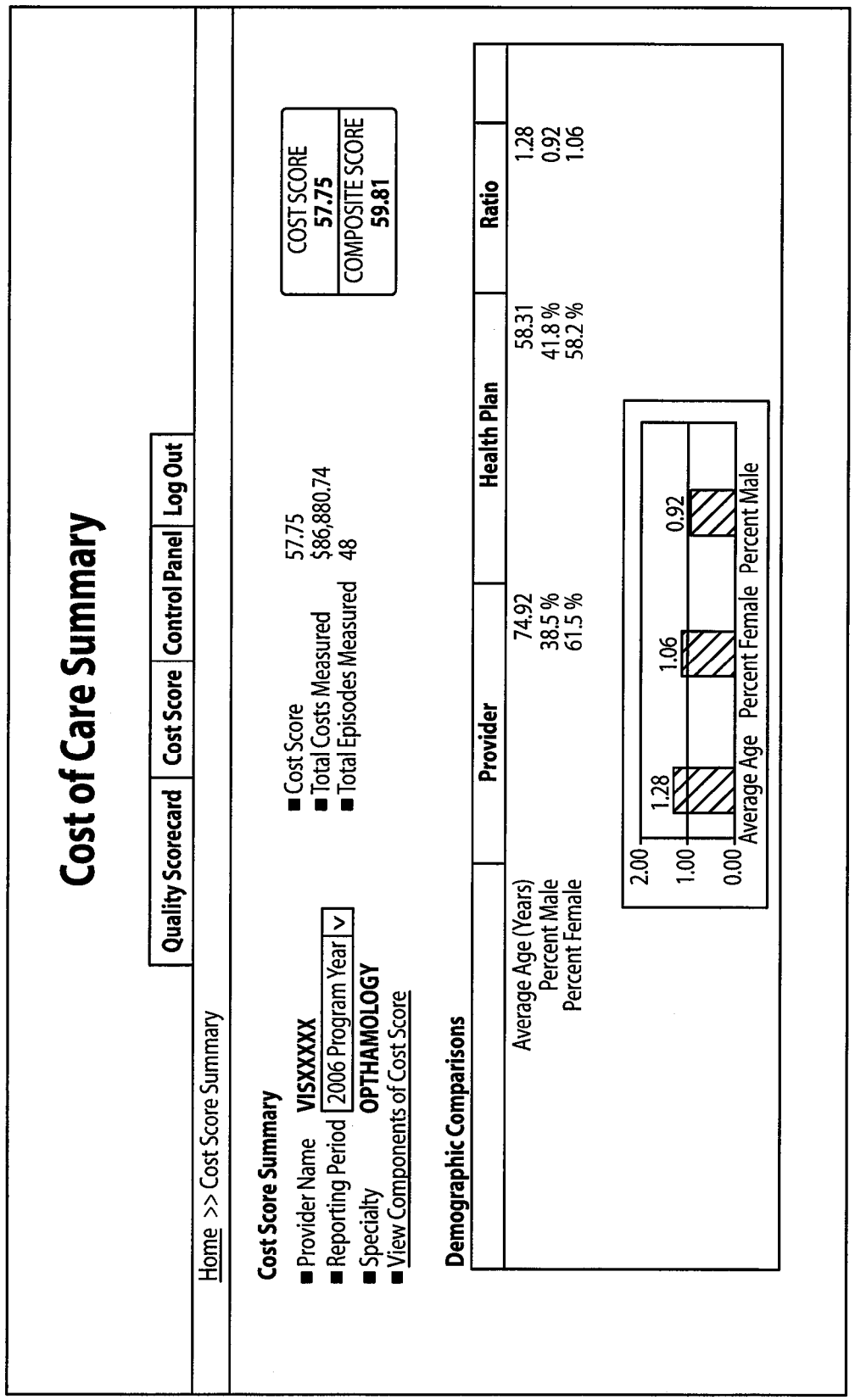

Referring now to FIG. 4, one example of the cost of care summary screen 304 is described. The screen 304 displays summary of information for a particular provider. For example, the average age, percentage male, and percentage female, of patients for a provider are shown and comparison of these statistics to other patients of the health plan is displayed. The ratio of provider to health plan is also provided and displayed. A cost score and a composite score are also shown.

Referring now to FIG. 5, one example of the cost of key episode screen 316 is described. The screen 316 shows various medical episodes and categorizes these episodes into most efficient, largest percentage of total costs, and least efficient. For example, it can be seen that a cataract episode was 36 percent of the costs and that there were a total of 9 of these episodes. The standardized cost score is a measure of efficiency. A score below zero indicates that utilization was below the expected cost and while a score above indicates that utilization was above expected and this relates to or is calculated by aggregating (a composite) of every episode treatment group.

Figure 6:
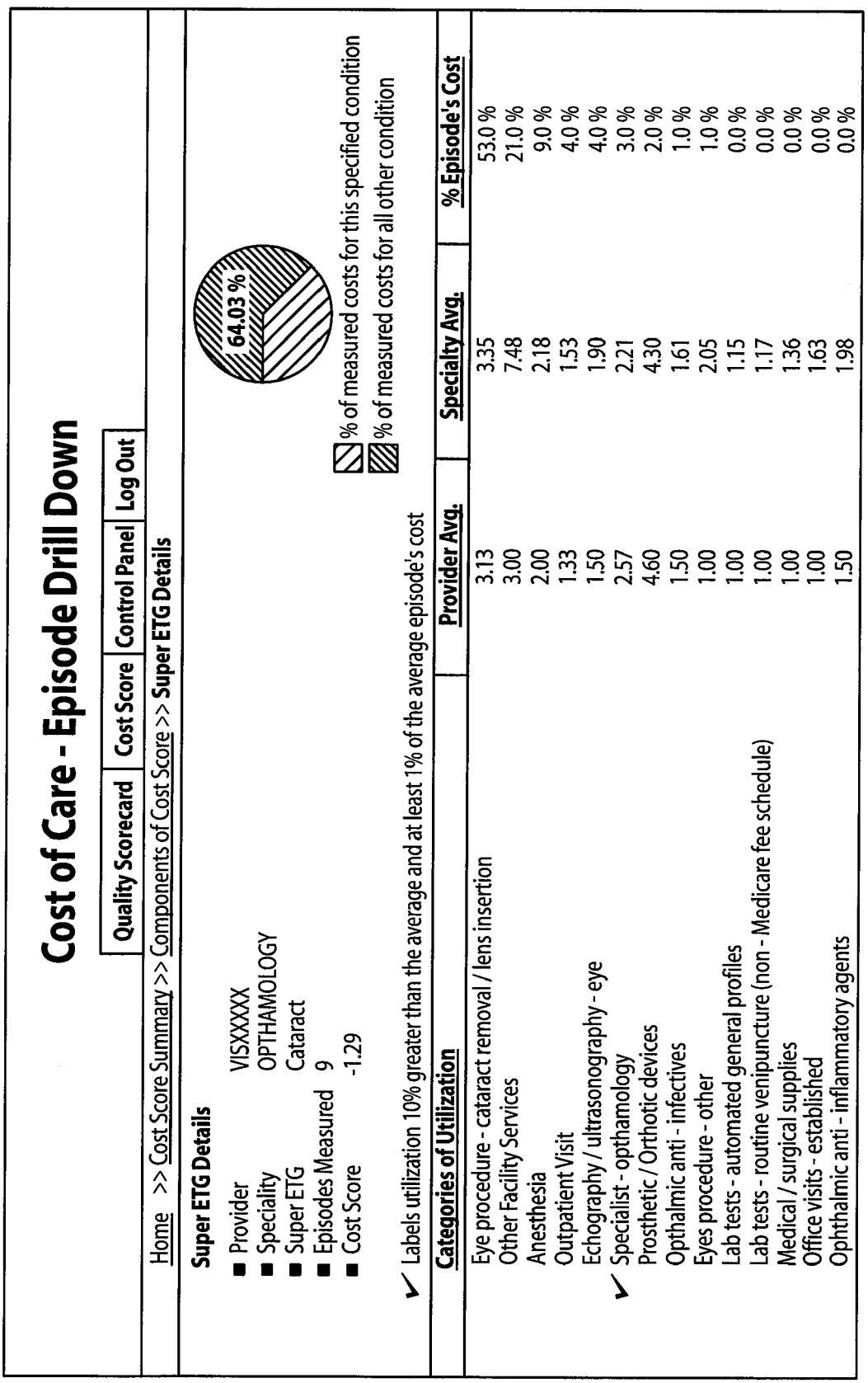

Referring now to FIG. 6, one example of the use of a drill down feature by a provider to obtain additional information is described. In this example, the provider selects the "cataract" link to receive more specific information related to the cataract procedure. The resultant screen of FIG. 6 shows specific cataract procedures. The cost and care module provide the capability to highlight categories of utilization where the provider deviates by a predetermined threshold from their peers.

Figure 7:
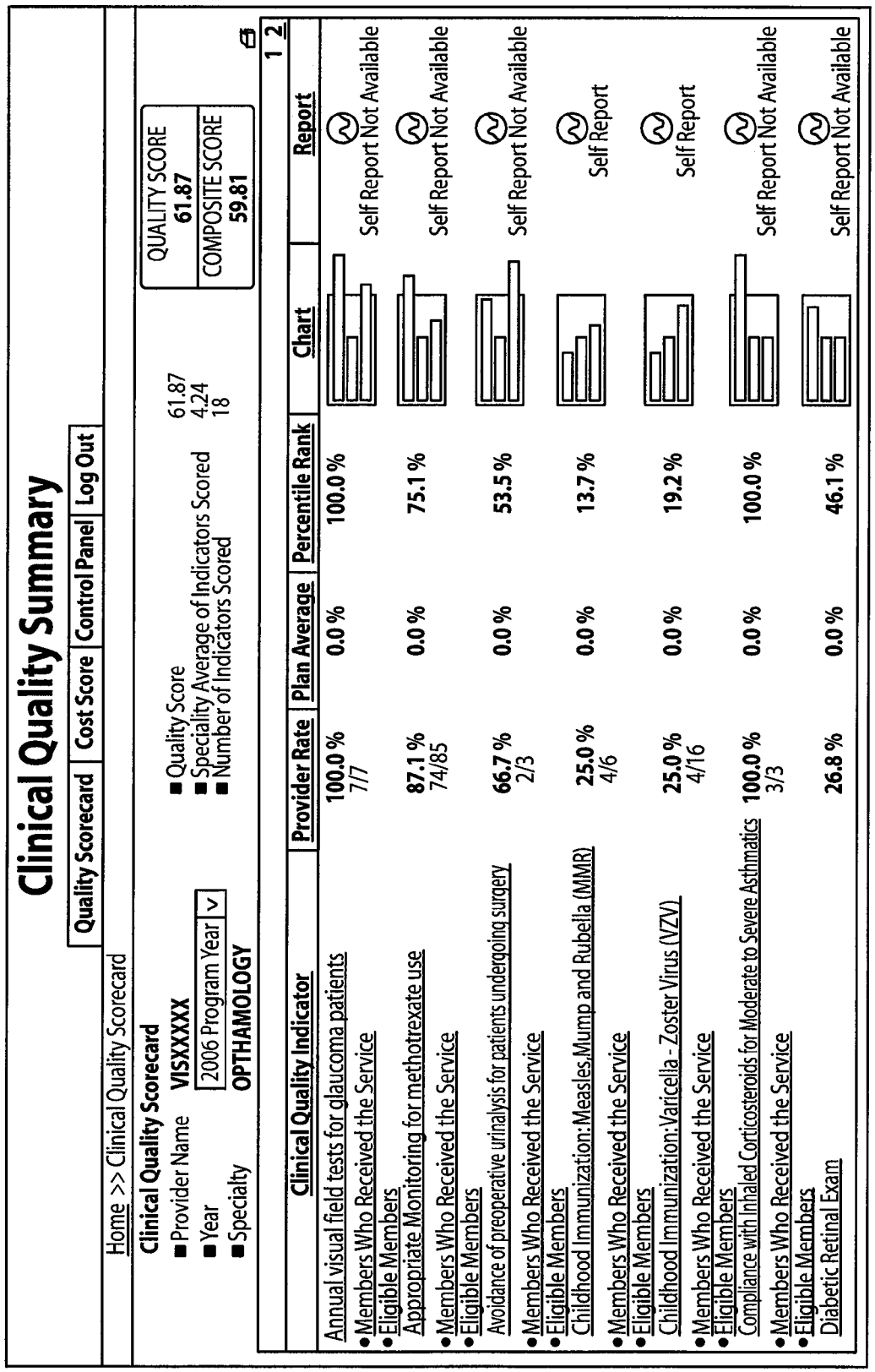

Referring now to FIG. 7, one example of the clinical quality summary screen 306 is described. Various indicators (metrics) are shown on the screen. A quality score is also shown as is the specialty average and the number of indicators (metrics) scored. Each metric has a link that when selected accesses a list of members who have received the service and another link that accesses a list of eligible members. The selection of a self-report link (if available) retrieves additional self-report screens and this allows for the self-report of data for a particular metric or indicator.

Figure 8:
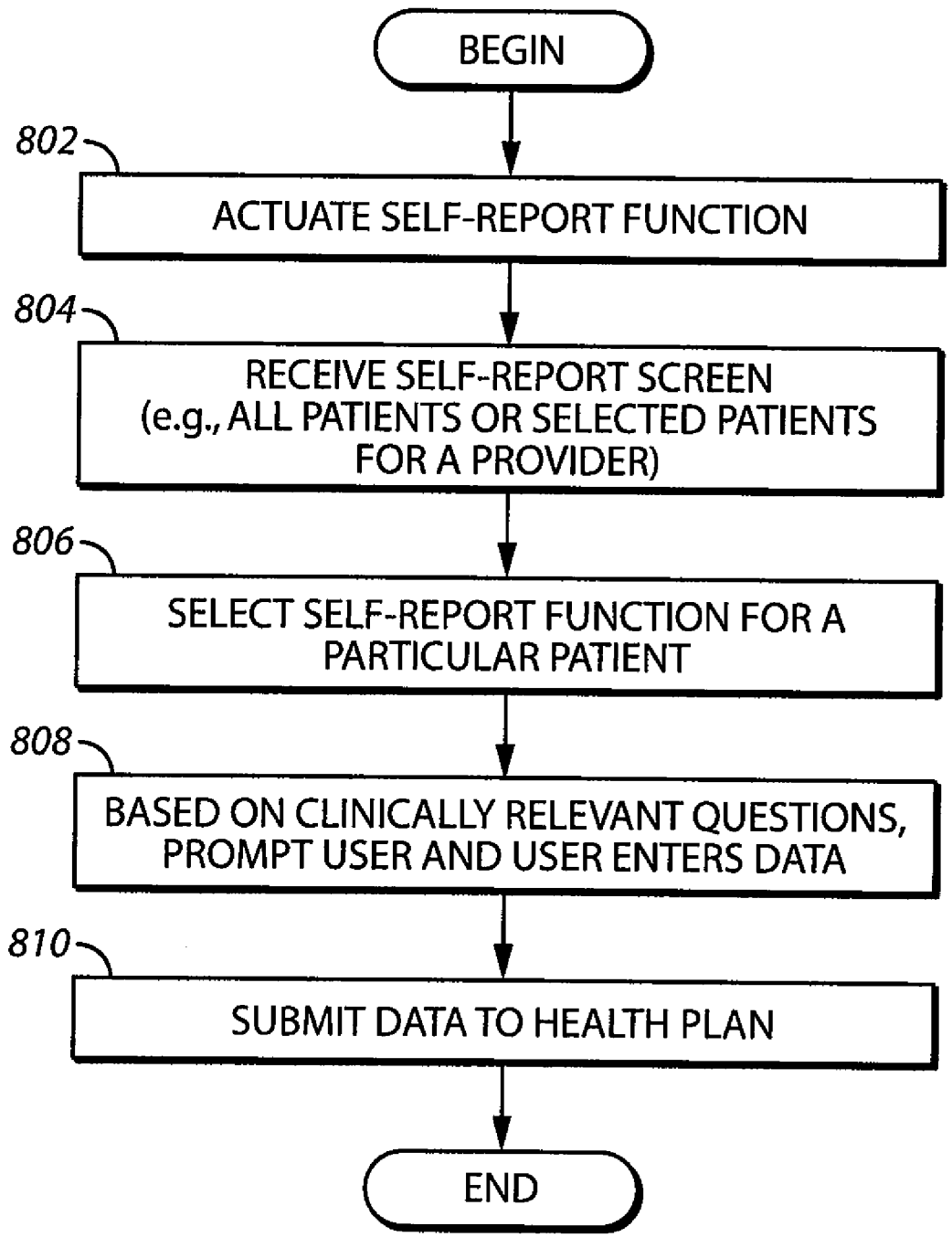
FIG. 8 comprises a flowchart of an approach for self-reporting data according to various embodiments of the present invention.

Referring now to FIG. 8, one example of an approach for self-reporting data is described. At step 802, a self-report function is actuated. For example, a health plan may alert a provider that there are gaps and service of patients of the provider. This may be done periodically (e.g., by sending email) or the provider may login to the system and initiate self-reporting. At step 804, a self-report screen is received by the provider. For example, a screen is presented to the provider that has a patient list. At step 806, a self-report function for a particular patient is selected by the provider. This may be done by selecting a link (e.g., button) on the screen and clicking on the link using a computer mouse.

At step 808, based on clinically relevant questions, the user enters self-report data. For example, the provider may be asked if they have given a vaccination to a patient or if not, the reason they did not provide the vaccination. At step 810, the self-report data is reported to the health plan. The self-report data may be presented and entered in a variety of different ways. For example, a series of yes/no or multiple choice questions may be presented to the provider and the provider may select a link (e.g., a box) on the screen to indicate the answer. In another example, the provider may enter text and this textual information is analyzed by the health plans. Examples of other entry approaches are possible. The health plan and/or some external entity may have access to the data for viewing and/or reassessment purposes.

Figure 9:
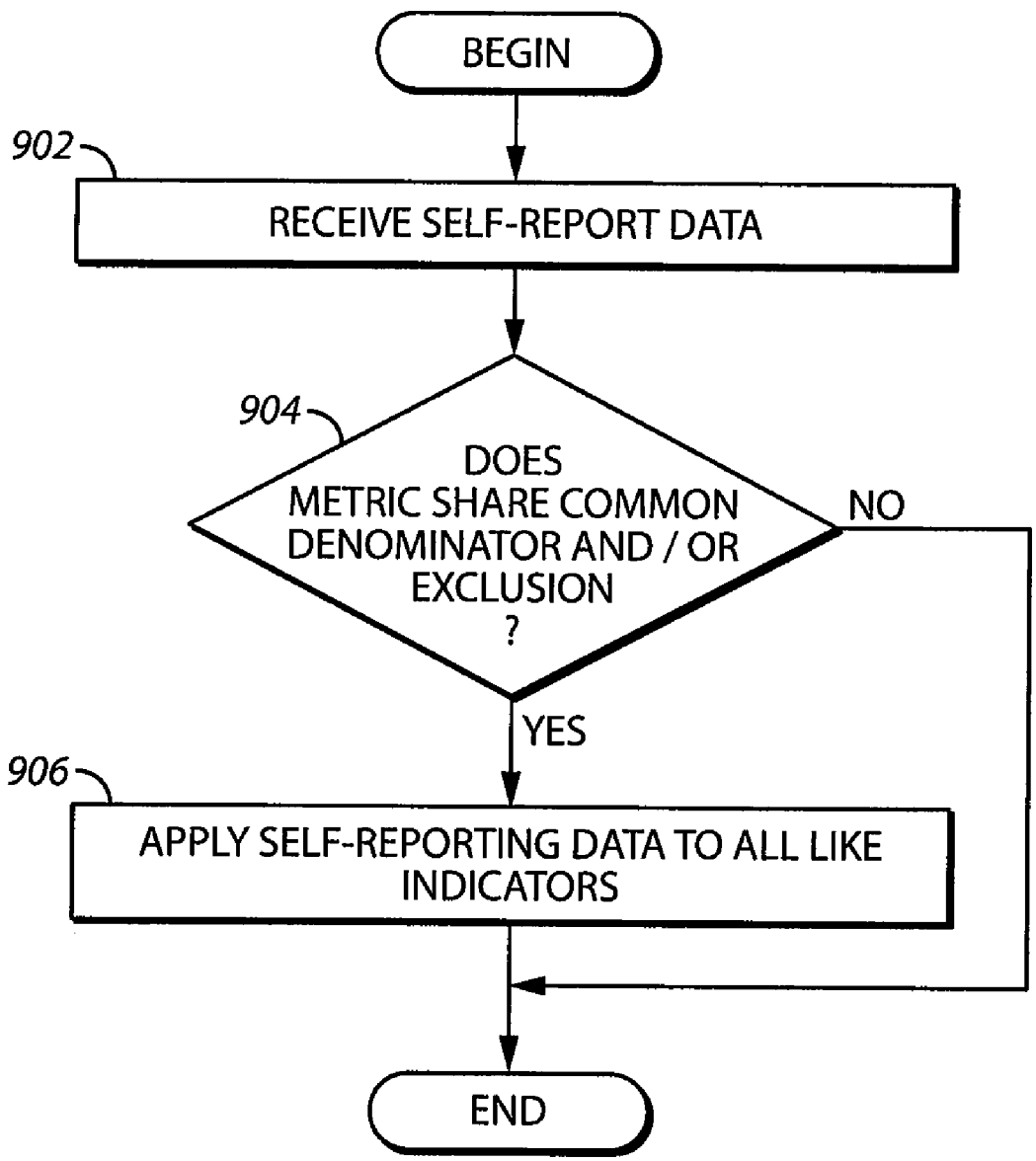
FIG. 9 comprises a flowchart showing an approach for linking medical metrics in the self-reporting system according to various embodiments of the present invention.

Referring now to FIG. 9, one example of linking metrics is described. At step 902, self-report data is received. At step 904, it is determined if the metric shares a common denominator and/or a common exclusion. For example, the common denominator may be diabetes patients and a common exclusion may be gestational diabetes. If the answer at step 904 is negative, then execution ends. If the answer is affirmative, at step 906 self-report data is applied to all like indicators, all like indicators related to the common denominator and/or common exclusions.

In one example of this approach, the MMR vaccination metric and the VZV vaccination metric may be linked together. The system will notify the provider that the same self-report data will be applied to a child patient if the child patient appears in or is associated with one of these like-metrics. For instance, if the provider enters a date of birth that makes the child patient ineligible to receive an MMR vaccination, the system will also remove the child patient from the VZV metric assessment. In another example, if the provider enters that the member had a valid exclusion (e.g., gestational diabetes), the member will be removed from all applicable diabetes metrics.

Figure 10:
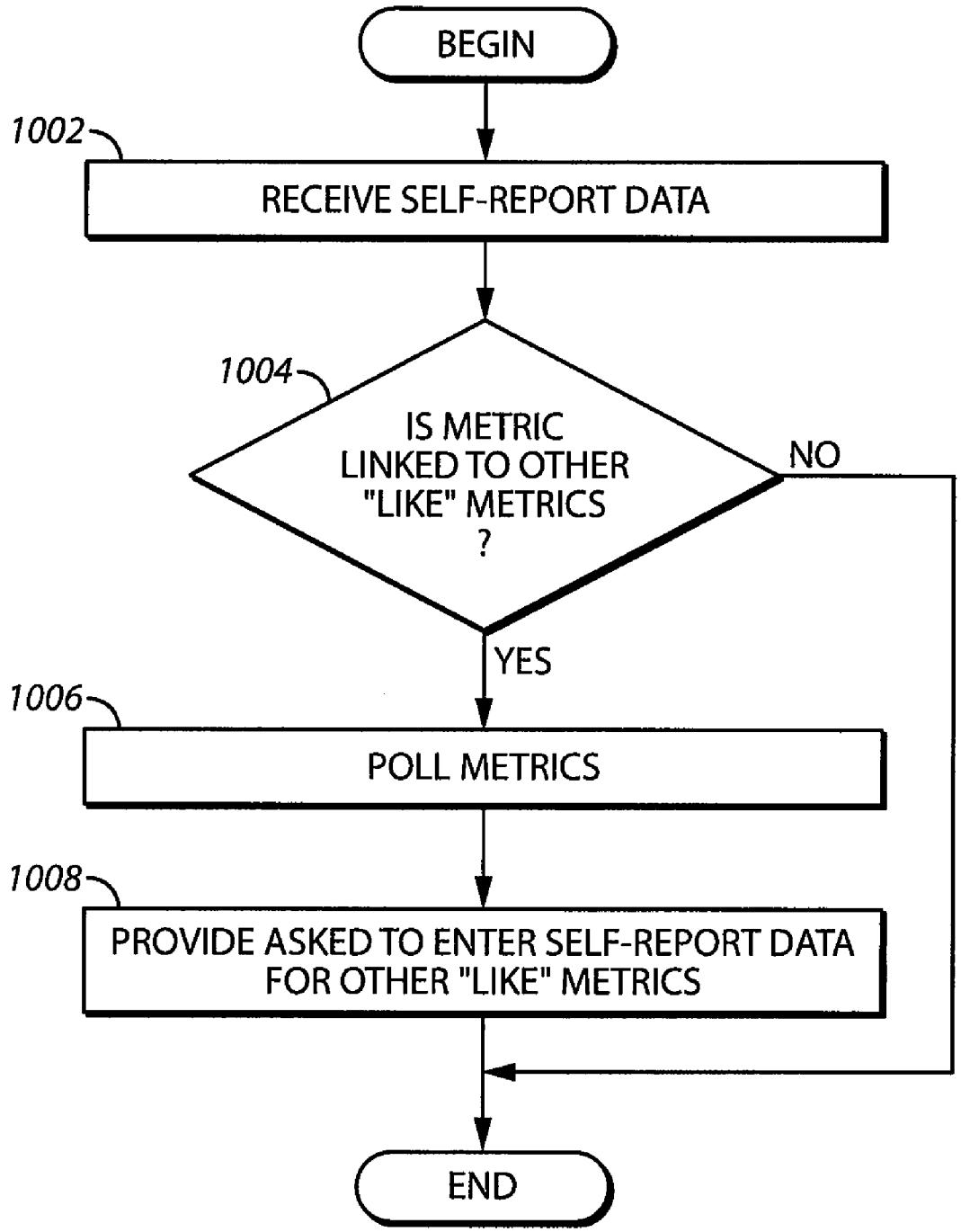
FIG. 10 comprises a flowchart of another approach for linking medical metrics in a self-reporting system according to various embodiments of the present invention.

Referring now to FIG. 10, another example of linking metrics is described. At step 1002, self-report data is received. At step 1004, it is determined whether the metric is linked to other like metrics. If the answer at step 1004 is negative, then execution ends. If the answer at step 1004 is affirmative, then at step 1006 like metrics are polled. At step 1008, the provider is asked to enter self-report data for other like metrics.

In one example of this approach, if a provider enters that a patient received an HbA1c test for the HbA1C testing for the diabetes metric, the system will search to see if the patient is a non-numerator hit for other diabetes measures and ask the provider if they wish to enter self-report data for these measures as well. In this example, the patient is a diabetes patient (e.g., a non-numerator hit). Consequently, the system will prompt the provider to see if the provider wishes to enter self-report data for other types of diabetes tests if a service gap for the patient is identified for any one of these metrics.

Referring now to FIGS. 11-16, examples of screen shots for the self-reporting of data are described. It will be understood that these are only examples of a sequence of screens a user can see and that other sequences are possible. It will also be understood that the contents of the screens (e.g., the links present) may also differ and that other examples are possible.

Figure 11:
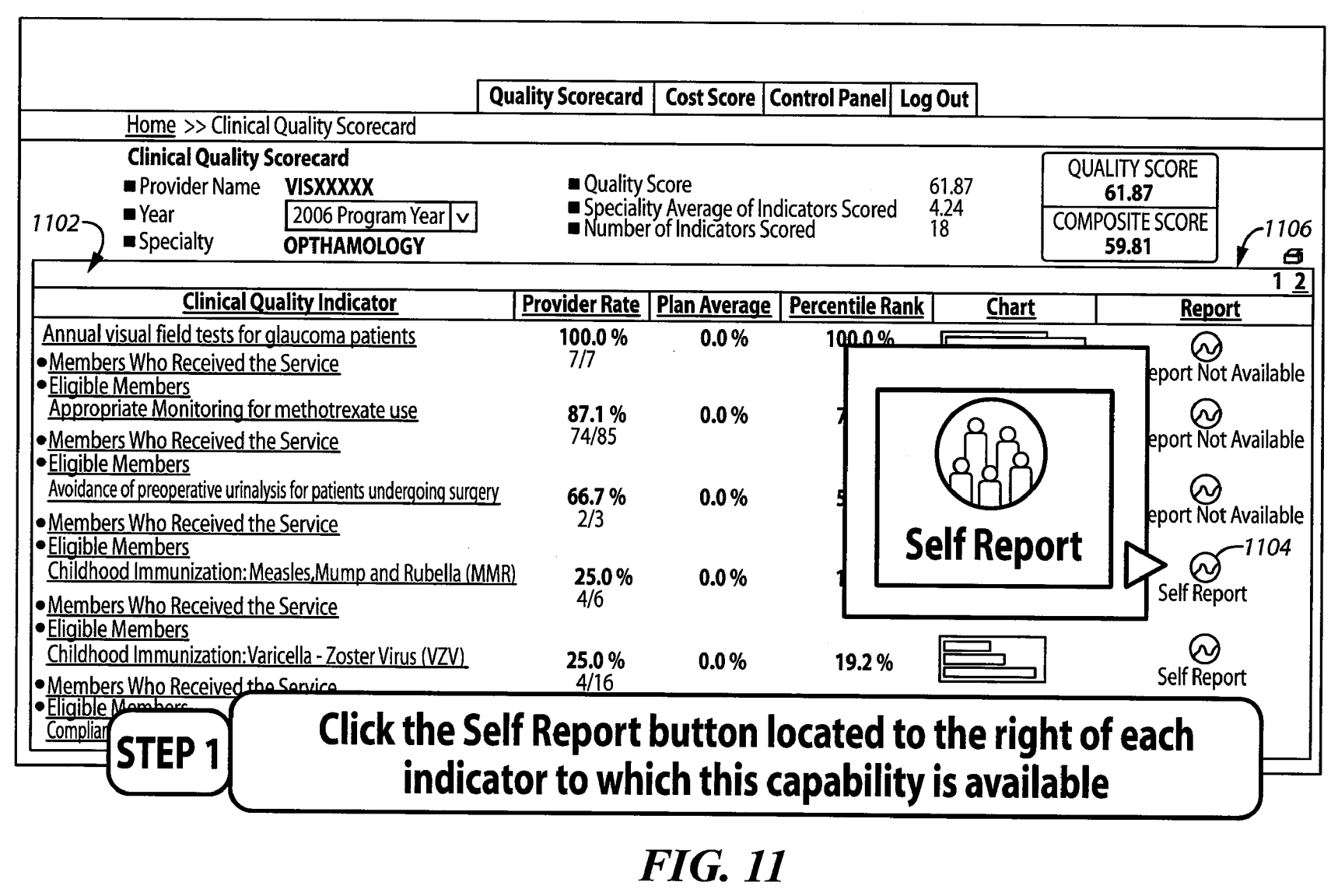

Referring now to FIG. 11, a screen where the self-report function may be selected is described. As shown, a list of services is presented to the provider (under a clinical quality indicator column 1102). Some of these services or metrics may allow for self-reporting while other examples may not allow self-reporting to occur. The provider selects an appropriate link 1104 (under a report column 1106) to self-report data for that particular metric (e.g., the metric in this case relates to childhood immunizations).

Referring now to FIG. 12, the result of selecting a self-report link 1104 in FIG. 11 is described. A list of all members who did not receive a service or procedure as defined by the quality indicator or metric is provided. The screen has a column for member identifier (the left most column 1202), a date of birth column 1204, a last name column 1206, and a first name of the patient column 1208. The provider selects the "Add self reporting data" link 1210 (i.e., in the right most column 1212) to enter data for a particular member. Additional information may be provided. For example, a date of service column may also be provided.

Referring now to FIG. 13, the result of selecting the "Add self report data" link of FIG. 12 is described. At this point, the provider is asked to confirm the date of birth and age of the member in fields 1302. The provider is allowed to correct the date of birth as it could impact member eligibility for the measure. The provider selects the "next" link 1304 to enter this information.

Referring now to FIG. 14, the result of entering the self-report information using the screen of FIG. 13 is described. As shown, the provider enters the appropriate information in the fields 1402. After the information is entered, the provider selects a next button 1404 to move to the next screen. It will be appreciated that the self-report information requested of the provider is customized to the metric, patient, and/or provider. In this example, the provider selects particular boxes to indicate self-report information. Other examples of screens that are customized according to different metrics are possible. It will also be appreciated that other data entry approaches may be used.

FIG. 15 shows the screen presented to the provider if the date of birth is correct and the provider confirms that services were not provided. With this screen, another option will be to enter data in the fields 1502 that the member met the denominator exclusion criteria. The provider may then select the next link 1504 to move to the next screen.

FIG. 16 shows a final confirmation screen presented to the provider that is needed to submit the data to the health plan for consideration. The screen has a field 1602 summarizing the self-report data and any linkages made by the system. The provider selects a select link 1604 to submit the self-report data to the health plan. Once the data is submitted it cannot be further modified by the provider.

Referring now to FIG. 17, a screen is shown that includes the recalculated assessment (i.e., the hybrid rate). The Clinical Quality Indicator includes link to specifications and member lists for each indicator that the provider received a score. The Administrative Rate is a performance rate calculated for the individual provider using administrative claims data as the underlying data source for analysis. The Hybrid Rate is a performance rate calculated for the individual provider using both administrative claims data and the data submitted through the self report system as the underlying data sources. The Plan Rate is the overall performance rate of the plan using administrative claims data as the underlying data source. The Quality Score is a percentile rank of the provider's score for quality performance based on a methodology that is defined in collaboration with the client. It also could be a simple absolute or a relative score. The Cost Score is a percentile rank of provider's score for cost of care performance based on a methodology that is defined in collaboration with the client. It also could be a simple absolute or a relative score. The Composite is a combined score that takes into consideration the providers quality and cost performance levels based on a methodology that is defined in collaboration with the client.

Thus, approaches are provided for the self-reporting of data from a medical provider that allows a provider assessment to be calculated and used. This self-reporting function provides for additional transparency for providers in seeing how their assessments are determined and allows a quick and convenient mechanism for these providers to update and improve their assessments. In so doing, the attractiveness of medical plans and provider participation in these plans are enhanced and increased. The self-reporting tool provided herein is convenient for providers to uses, does not require providers to purchase or install additional or costly software, and is available all the time. These approaches are also secure to use and provide for the display and retrieval of patient records.

Those skilled in the art will recognize that a wide variety of modifications, alterations, and combinations can be made with respect to the above described embodiments without departing from the spirit and scope of the invention, and that such modifications, alterations, and combinations are to be viewed as being within the scope of the invention.

What is claimed is:

1. A method of providing an accurate assessment for a medical provider comprising:

storing a plurality of medical records at an electronic data storage device;

at an electronic processing device, selecting at least one medical record from the plurality of medical records, the at least one medical record being associated with a medical patient, the at least one medical record having an associated initial performance assessment associated with the medical provider who provided medical services associated with the at least one medical record to the medical patient, the initial assessment being determined at the electronic processing device and stored at the electronic data storage device;

at the electronic processing device, identifying gaps in service associated with the selected record;

in real time and at an electronic presentation device, presenting at least portions of the at least one medical record to the provider;

at an electronic user interface associated with the electronic presentation device receiving supplemental information from the provider, the supplemental information relating to the medical patient and including information at least partially filling the identified gaps in service;

transmitting the supplemental information from the electronic user interface to the processing device over a communication link;

at the electronic processing device, receiving the transmitted supplemental information and automatically and in real-time re-calculating the assessment using the supplemental information without the need for a third-party to approve the reassessment.

2. The method of claim 1 further comprising analyzing the at least one medical record, forming at least one inquiry for the provider based upon the analyzing, and presenting the at least one inquiry to the provider.

3. The method of claim 1 further comprising applying a time limit during which the provider is allowed to supplement the information.

4. The method of claim 1 further comprising establishing a secure communication link with the provider.

5. The method of claim 4 wherein establishing a secure connection comprises requiring the provider to supply a password before communications via the communication link are allowed.

6. A system comprising:

an electronic database configured to store on a computer medium at least one patient record and an initial performance assessment related to the at least one patient record;

an electronic interface having an output and an input, the electronic interface being configured to receive self-reported medical data from at least one medical service provider via an Internet-based communication link;

an electronic self-reporting module coupled to the interface and the database, the electronic self-reporting module configured to receive the at least one patient record from the electronic data base and determine at least one inquiry for a medical provider at the output of the electronic interface based upon analyzing the at least one patient record, the self-reporting module being further configured to identify gaps in patient service based upon analyzing the at least one patient record;

an electronic performance evaluation module coupled to the electronic database, the electronic interface, and the electronic self-reporting module, the electronic performance evaluation module configured to calculate the initial performance assessment and to determine an updated assessment of the initial assessment without the need for a third-party to approve the updated assessment the updated assessment based upon the self-reported medical data received at the input of the interface, the self-reported medical data being received from the provider in response to the at least one inquiry and including data that at least partially fills the identified service gaps.

7. The system of claim 6 wherein the communication link comprises a secure connection.

8. The system of claim 7 wherein the secure connection is established by the use of a password supplied by the provider.

9. The system of claim 6 wherein the performance evaluation module allows receipt of self-reported medical data from the provider for a predetermined length of time.

10. The system of claim 6 wherein the self-reporting module provides customized screens to the provider.

* * * * *